United States Patent [19]

Weber et al.

[11] Patent Number: 4,756,849

[45] Date of Patent: Jul. 12, 1988

[54] DETERGENTS CONTAINING ADDITIVES FOR PREVENTING THE TRANSFER OF DYES AND BRIGHTENERS

[75] Inventors: Rudolf Weber, Duesseldorf; Winfried Pochandke, Baumberg; Hans Andree, Leichlingen, all of Fed. Rep. of Germany

[73] Assignee: Henkel Kommanditgesellschaft auf Aktien, Duesseldorf, Fed. Rep. of Germany

[21] Appl. No.: 864,174

[22] Filed: May 16, 1986

[30] Foreign Application Priority Data

May 25, 1985 [DE] Fed. Rep. of Germany ....... 3519012

[51] Int. Cl.[4] .................................... C07C 5/54

[52] U.S. Cl. .................................... 252/542; 252/524; 252/528; 252/174.21; 252/174.25; 252/547; 252/140; 252/102

[58] Field of Search .................. 252/547, 528, 174.21, 252/174.25, 542, 524, 140, 102

[56] References Cited

U.S. PATENT DOCUMENTS 4,228,042 10/1980 Letton et al. ...................... 252/528
4,261,869 4/1981 Bishop et al. ...................... 252/547

FOREIGN PATENT DOCUMENTS 1224698 9/1966 Fed. Rep. of Germany .
2916656 11/1980 Fed. Rep. of Germany .
1348212 3/1974 United Kingdom .

*Primary Examiner*—Josephine Barr
*Attorney, Agent, or Firm*—Ernest G. Szoke; Henry E. Millson, Jr.; Real J. Grandmaison

[57] ABSTRACT

A detergent for washing mixtures of colored and white or light colored fabrics comprising a mixture of a monionic surfactant, a completely or partially water-soluble polyvinyl pyrrolidone polymeric constituent, a water-soluble cationic compound, a builder salt and other standard detergent ingredients. The detergent is substantially free of anionic-active compounds and strong electrolytes and is effective in preventing the transfer of dyes and optical brighteners between fabrics during washing.

11 Claims, No Drawings

DETERGENTS CONTAINING ADDITIVES FOR PREVENTING THE TRANSFER OF DYES AND BRIGHTENERS

BACKGROUND OF THE INVENTION

1. Field of the Invention

The present invention relates to detergents based on nonionic surfactants containing a combination of a polyvinyl pyrrolidone polymeric constituent and a cationic compound which counteract the transfer of dyes and brighteners from colored or brightened fabrics to white, light-colored or non-brightened fabrics when such fabrics are laundered together.

2. Description of Related Art

The transfer of dyes and brighteners that occurs when washing mixed loads of colored and white fabrics or colored and light-colored fabrics is a well-known problem to which several solutions have already been proposed. Unfortunately, none of these solutions has been entirely satisfactory, either because the cleaning agents have only a limited effect on a large number of dyes and fabrics in use today or because the agents only counteract the transfer of either the dye or the brightener, but not both.

Great Britain Patent No. 1,348,212 describes a built detergent having a discoloration-inhibiting additive consisting of a homopolymer or copolymer of polyvinyl pyrrolidone. According to the teachings of this patent, the detergent contains a nonionic surfactant and from about 5 to about 40% by weight of the partially or completely water-soluble homopolymer of vinyl pyrrolidone or a copolymer of vinyl pyrrolidone and a suitable monomer, based on the weight of nonionic surfactant and vinyl pyrrolidone polymer.

German Patent Application No. 29 16 656 describes detergents containing alkylpyridinium salts for preventing transfer of optical brighteners from brightener-containing fabrics to brightener-free fabrics during the washing process. The detergents contain from 0.5 to 10% by weight of the alkylpyridinium salt, based on the detergent as a whole.

It is also known from German Patent Application No. 12 24 698 that fabrics, discolored because of the transfer of brighteners, can be treated with a solution of tertiary, quaternary or branched-chain organic nitrogen bases, or salts thereof, to regenerate their color.

DESCRIPTION OF THE INVENTION

It has now been found that detergents containing a mixture of a nonionic surfactant, a partially or completely water-soluble vinyl pyrrolidone polymeric constituent, a detergent builder and other standard detergent ingredients, the detergents being substantially free from anionic-active (anionic surfactant) compounds, are highly effective in preventing the transfer of both dyes and optical brighteners providing these detergents also contain a small quantity of a water soluble, quaternary nitrogen-containing cationic compound and are substantially or completely free of electrolytes. This discovery is quite surprising since even an extremely small amount of the quaternary nitrogen-containing cationic compound in the presence of the vinyl pyrrolidone polymeric constituent prevents the transfer of dyes and optical brighteners to a far greater extent than would have been expected from the prior art, i.e. than one would have expected from use of the water-soluble polymeric constituent alone or from use of the water-soluble cationic compound alone.

The detergent of the present invention includes as essential constituents a nonionic surfactant, a partially or completely water-soluble polyvinyl pyrrolidine polymeric constituent, a builder salt and a water-soluble cationic compound. Other than in the operating examples, or where otherwise indicated, all numbers expressing quantities of ingredients or reaction conditions used herein are to be understood as modified in all instances by the term "about."

A wide variety of known nonionic surfactants can be used. Particularly suitable nonionic surfactants are those derived from the reaction between $C_8$–$C_{24}$ alcohols with an alkylene oxide. The alcohols may be of natural or synthetic origin, they may have a linear or branched structure, and they may be saturated or unsaturated. A preferred class of nonionic surfactants are prepared by reacting an oxoalcohol and/or a fatty alcohol with from 2 to 20 moles of an alkylene oxide per mole of alcohol. In general, the alkylene oxide is ethylene oxide and/or propylene oxide. Ethylene oxide is preferred. Particularly good results are obtained using nonionic surfactants derived from fatty alcohols-coconut oil fatty alcohol and tallow fatty alcohols being preferred. To obtain particularly well-balanced properties in the detergent formulation, it often is desirable to use a combination of these fatty alcohol alkoxylates having differing degrees of alkoxylation.

Generally, the detergent will contain anywhere from about 5 to 50% by weight of the nonionic surfactant, preferably from about 10 to 20% by weight.

The next component of the detergent is the partially or completely water-soluble vinyl pyrrolidone polymeric constituent. The vinyl pyrrolidone polymeric constituent includes homopolymers and/or copolymers of vinyl pyrrolidone having a molecular weight in the range of from about 10,000 to about 1,000,000. Preferred homopolymers have a molecular weight of from about 15,000 to about 700,000. In copolymers suitable for detergents according to the present invention, the vinyl pyrrolidone comprises at least about 50 mol % of the copolymer. Suitable comonomers are, for example, vinyl acetate, acrylonitrile and maleic acid anhydride. The molecular weight of the copolymers is preferably in the range of from about 20,000 to about 200,000.

The vinyl pyrrolidone polymeric constituent generally comprises from about 0.5 to 8% by weight of the detergent of the present invention, based on the detergent as a whole. Particularly good results are obtained with detergents containing from 1 to 4% by weight of the polymer based on the vinyl pyrrolidone polymeric constituent.

Another important constituent of the detergent of the present invention is a detergent builder. The detergent builder may be present in the detergent in a quantity of up to about 50% by weight, based on the detergent as a whole. Suitable inorganic detergent builders for use in the present invention include the water-soluble alkali metal silicates, carbonates, and borates and the alkali alumosilicates of the A, X, Y and P type zeolites. In addition to these inorganic builders, it also is possible to use polymeric organic detergent builders. Examples of suitable polymeric builders include polyacrylic acid optionally modified with maleic acid anhydride and copolymers of vinyl acetate and maleic acid anhydride. Commercial organic builders are sold by BASF, AG, Ludwigshafen, Germany, under the trademarks Sokalan TM CP 5 and Sokalan TM CP 2. Builders such as these are generally present in a quantity of up to about 30% by weight, preferably in a quantity of up to 15% by weight. The detergent builder, however, must not be a strong electrolyte. An important feature of the detergent of the present invention is that it is substantially or completely free of strong electrolytes. In the context of the present invention, the term "strong electrolyte" is understood to be a salt of a strong base and a strong acid. Water-soluble builder salts are the most common examples of strong electrolytes which often are added to detergents. Specific examples of strong electrolytes which are used as builder salts are alkali phosphates, sulfates and sulfonates. Strong electrolytes should only be present in the detergent of the present invention in a quantity of at most about 10% by weight.

The last constituent of the detergent of this invention is the water-soluble quaternary nitrogen-containing cationic compound. Suitable water-soluble cationic compounds include:

(a) quaternary ammonium compounds represented by the following general formula:

$$R^1{}_m R^2{}_n N^{(+)} X^{(-)} \qquad (I)$$

in which $R^1$ is an alkyl, alkenyl, acyloxyethyl, benzyl or hydroxylalkyl group containing from 8 to 20 carbon atoms; $R^2$ is an alkyl group containing from 1 to 4 carbon atoms; $m+n=4$, with the proviso that, where $R^1$ contains from 8 to 13 carbon atoms, $m=1$ or 2 and, where $R^1$ contains from 14 to 20 carbon atoms, $m=1$, and $X^{(-)}$ in an anion establishing the electroneutrality of the quaternary ammonium compound;

(b) imidazolinium compounds represented by the following general formula:

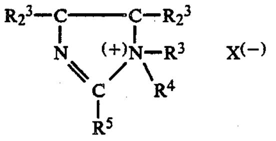

(II)

in which $R^3$ is a hydrogen atom or an alkyl group, optionally substituted, containing from 1 to 18 carbon atoms; $R^4$ is an alkyl or alkenyl group containing from 10 to 20 carbon atoms or an alkylamidoethyl or alkenylamidoethyl group containing from 10 to 20 carbon atoms in the alkyl or alkenyl moiety and $R^5$ is an alkyl or alkenyl group containing from 10 to 20 carbon atoms and $X^{(-)}$ is as defined above; and (c) alkylpyridinium salts containing from 10 to 18 carbon atoms in the alkyl group.

The cationic compounds of formula (I), which are used in combination with the vinyl pyrrolidone polymeric constituent, are quaternary ammonium compounds containing one or two alkyl, alkenyl, acyloxyethyl, benzyl or hydroxyalkyl groups containing from 8 to 12 carbon atoms and, for the remaining substituents, alkyl groups containing from 1 to 4 carbon atoms. Quaternary ammonium compounds of formula (I) containing a $C_{14}$-$C_{20}$ alkyl or alkenyl group and, for the remaining substituents, three $C_1$-$C_4$ alkyl groups also are suitable. In other words, $R^1$ is an alkyl, alkenyl, acyloxyethyl, benzyl or hydroxyalkyl group containing from 8 to 20 carbon atoms, and $R^2$ is an alkyl group containing from 1 to 4 carbon atoms, with the proviso that, where $R^1$ contains from 8 to 13 carbon atoms m equals 1 or 2 and n equals 3 or 2 respectively and where $R^1$ contains from 14 to 20 carbon atoms, $m=1$ and $n=3$. $R^1$ preferably contains an even number of carbon atoms in the range of 8 to 20. Thus where $R^1$ preferably contains an even number of from 8 to 12 carbon atoms, m equals 1 or 2 and n equals 3 or 2 respectively and where $R_1$ contains an even number of from 14 to 20 carbon atoms, $m=1$ and $n=3$. $X^{(-)}$ is an anion establishing the electroneutrality of the quaternary ammonium compound. Suitable anions $X^{(-)}$ include, for example, chloride, bromide or hydrogen sulfate.

Examples of suitable quaternary ammonium compounds corresponding to formula (I) are dioctyl dimethyl ammonium chloride, octyl dodecyl dimethyl ammonium chloride, hexadecyl trimethyl ammonium chloride or bromide, hexadecyl dimethyl benzyl ammonium chloride, distearyl or dihydrotallow alkyl dimethyl ammonium chloride, methyl ditallowalkyl hydroxypropyl ammonium chloride, didecyl methyl ethyl ammonium chloride, didodecyl dimethyl ammonium hydrogen sulfate, dodecyl or tetradecyl trimethyl ammonium bromide or chloride, tallowalkyl trimethyl ammonium chloride and octadecyl trimethyl ammonium hydrogen sulfate.

The alkyl group of alkylpyridinium salts suitable for use as the water-soluble, quaternary nitrogen-containing cationic compound of the present invention typically contains from 10 to 18 carbon atoms, and preferably from 12 to 16 carbon atoms in the alkyl group. The cationic compound generally comprises from 0.01 to 2% by weight of the detergent, based on the detergent as a whole. Also the water-soluble polyvinyl pyrrolidone polymer is always present in the detergent in a larger quantity than the cationic compound. For example, a detergent containing 1 to 4% by weight of the polymeric constituent and from 0.01 to 0.5% by weight of an alkyl pyridinium salt, the weight ratio of polymeric constituent to pyridinium salt preferably being from 10:1 to 50:1 and more preferably from 30:1 to 40:1, is particularly preferred.

An important factor in preventing transfer of dyes and brighteners when using detergents of the present invention is the substantially complete absence of anionic-active compounds, such as anionic surfactants of the sulfate, sulfonate or acylcyanamide type, alkali salts of fatty acids, anionic-active dyes and anionic-active optical brighteners. It is important that the detergents of the present invention contain substantially no anionic-active compounds since these compounds impair the effect of the cationic compounds added in accordance with the invention.

In addition to the nonionic surfactant(s), the polyvinyl pyrrolidone polymer, the detergent builder and the cationic compound, the detergents of the present invention may also contain other standard detergent ingredients. These ingredients may be in the form of powders, granules, liquids or pastes according to the composition of the detergent. Other standard detergent ingredients include, for example, bleaches (such as the perhydrates including sodium perborate monohydrate or tetrahydrate, sodium percarbonate, sodium perpyrophosphate, sodium persilicate and the perhydrates of urea), bleach activators and stabilizers (including poly-N-acyl and poly-O-acyl compounds such as tetraacetyl methylene diamine, tetraacetyl ethylene diamine, tetraacetyl glycoluril, sodium cyanamide, N-alkyl-N-sulfonylcarbonamides, N-acylhydantoins, N-acylated cyclic hydrazides, triazoles, urazoles, diketopiperazines, sulfurylamides, cyanurates, imidazolines and glucose pentaacetate), heavy metal complexing agents (including complexing agents of the aminopolycarboxylic acid and polyphosphonic acid types, such as ethylene diamine tetraacetic acid (EDTA), 1-hydroxyethane-1,1-diphosphonic acid, diethylene triamine pentaacetic acid, aminotri-(methylenephosphonic acid), ethylene diamine tetra-(methylene-phosphonic acid and diethylene triamine tetra-(methylenephosphonic acid)), enzymes (including proteases, lipases and amylases, especially those obtained from bacterial and fungi strains such as *Bacillus subtilis, Bacillus, licheniformis* and *Streptomyces griseus*), foam regulators (including organopolysiloxanes, silanized silica, paraffins, waxes, saturated $C_{18}$–$C_{24}$ fatty acids and alkali soaps thereof), soil suspending agents, purfumes, non-anionic dyes, preservatives, fillers and, especially for liquid or paste-like formulations, hydrotropic agents, opacifiers, viscosity regulators, organic solvents and water.

Accordingly, a typical detergent according to the present invention might have a composition within the following ranges:

(a) from 10 to 20% by weight of a nonionic surfactant prepared by reacting tallow fatty alcohol with 5 to 15 moles of ethylene oxide per mole of alcohol,
(b) from 1 to 4% by weight polyvinyl pyrrolidone,
(c) from 0.01 to 0.5% by weight of a $C_{12}$–$C_{16}$ alkylpyridinium salt,
(d) from 0.1 to 3% by weight foam inhibitor,
(e) from 0.5 to 4% by weight Na and/or Mg silicate,
(f) from 10 to 40% by weight sodium alumosilicate,
(g) from 10 to 30% by weight sodium perborate,
(h) from 0.5 to 2.5% by weight heavy metal complexing agent,
(i) from 0.5 to 3% by weight cellulose derivatives,
(j) from 0.1 to 1% by weight enzymes,
(k) from 0.01 to 0.5% by weight perfumes, with the balance comprising water and substantially inert fillers.

Detergents of the present invention not only exhibit excellent detergency with respect to fatty and pigment-like soil, but they are also extremely effective in suppressing the transfer of dyes from colored fabrics and of optical brighteners from fabrics treated with brighteners to non-colored or light-colored fabrics or to fabrics which have not been treated with brighteners. Thus, errors in sorting colored from non-colored fabrics before washing will not result in undesirable discoloration or dye transfer between the fabrics. In addition, the mixed washing of brightened and non-brightened fabrics does not lead to any discoloration caused by brightener transfer. Detergents of the present invention may also be utilized with advantage in the manufacture of textile fabrics, for example in the finishing operation after dyeing or printing.

Detergents of the present invention act to suppress dye and brightener transfer to a much greater extent than would be expected from the quantity of (i) the water-soluble polyvinyl pyrrolidone polymer and (ii) the water-soluble quaternary nitrogen-containing cationic compound, contained in the detergents. Thus, there appears to be a synergistic increase in the dye/brightener transfer suppression properties of the detergent as a result of combining the water-soluble polyvinyl pyrrolidone polymer with a small quantity of a water-soluble cationic compound.

Furthermore, commensurate with the other ingredients, detergents of the present invention exhibit desirable detergent properties corresponding to those ingredients. Accordingly, the detergents are effective, for example, in removing bleachable soil, proteinaceous or starch-containing soil, and exhibit desirable foaming behavior during both hand and machine washing.

Although certain embodiments of the invention have been selected for description in the example hereinafter, it will be appreciated by this skilled in the art that this example is merely illustrative of, but does not in any way limit, the scope of the present invention which is defined in the appended claims.

EXAMPLE 1

A detergent A having the following composition was prepared (all percentages are percent by weight):

10.5% adduct of tallow fatty alcohol and 5 moles ethylene oxide
4.5% adduct of tallow fatty alcohol and 14 moles ethylene oxide
1% carboxymethyl cellulose
35% zeolite A
20% Na perborate
2.5% Na silicate
1% Mg silicate
0.2% EDTA (ethylene diamine tetraacetic acid)
1.35% HEDP (hydroxyethane diphosphonic acid), Na salt
0.3% enzyme
0.15% perfume
4% polyvinyl pyrrolidone
0.08% $C_{12}$–$C_{16}$ alkylpyridinium chloride balance comprising sodium carbonate and water.

Detergent A according to the invention was compared with: (1) a state-of-the-art detergent B, in which the $C_{12}$–$C_{16}$ alkylpyridinium chloride was replaced with sodium carbonate; (2) a detergent C, in which the polyvinyl pyrrolidone was replaced with sodium carbonate; and (3) a detergent D in which both the polyvinyl pyrrolidone and the alkyl pyridinium salt were replaced with sodium carbonate.

In an automatic tumbler-type washing machine (Siwamat 738), 3.5 kg of colored laundry and pieces of fabric which had been dyed with naphthol dyes, reactive dyes and non-after-treated dyes and soiled with artificial soil were washed twice in a two-step process at 60° C. (German water hardness of 16° dH) using 140 g of detergent for the preliminary wash and 140 g of detergent for the main wash. After washing, the remission values (R values) were measured against white fabrics (cotton, polyester/cotton, polyamide, polyacrylonitrile and polyester). Higher R values indicate improved dye/brightener transfer suppressing ability.

The following results were obtained:

TABLE 1

| Detergent | R Value |
|---|---|
| A (Detergent according to the invention) | 74.8 |
| B (State-of-the-art detergent) | 72.7 |
| C (Detergent containing no polyvinyl pyrrolidone) | 71.3 |
| D (Detergent containing neither polyvinyl pyrrolidone nor alkylpyridinium salt) | 70.8 |

The highest R value was exhibited by terry cloth washed with detergent A. An addition of only 0.08% by weight of alkylpyridinium chloride to detergent A produced an increase in the R value of 2.1 units over detergent B (which had the same composition as detergent A, except the alkylpyridinium chloride was replaced by sodium carbonate). A comparison of detergents C and D shows that an increase in the R value of only about 0.5 units would be expected from the addition of 0.08% by weight alkylpyridinium chloride in the absence of the polyvinyl pyrrolidone.

The differences in the prevention of dye transfer of detergents A through D, as characterized by their R values, were clearly discernible to the naked eye.

Although the present invention has been described in terms of a number of specific embodiments and an example thereof, it will be appreciated by those skilled in the art that a wide variety of equivalents may be substituted for the specific parts and steps of operation described herein, all without departing from the spirit and scope of the present invention, as defined in the appended claims.

What is claimed is:

1. In a fabric detergent composition comprising from about 5 to about 50% by weight of a nonionic surfactant and up to about 50% by weight of a detergent builder; the improvement comprising the combination as a dye and brightener transfer surpressing component, (1) from about 0.5 to about 8% by weight of a partially or completely water-soluble vinyl pyrrolidone polymeric constituent having a molecular weight in the range of from about 10,000 to about 1,000,000, and (2) from about 0.01 to about 2% by weight of a water-soluble quaternary nitrogen-containing cationic compound comprising (a) $C_{10}$–$C_{18}$ alkylpyridinium salt;

all weights being based on the weight of said detergent composition, and wherein said detergent composition is free of anionic surfaceactive compound and strong electrolyte.

2. A detergent composition as in claim 1 wherein the weight ratio of said pyrrolidone polymeric constituent to said cationic compound is in the range of from about 10:1 to about 50:1.

3. A detergent composition as in claim 1 comprising from about 1 to about 4% by weight of said water-soluble vinyl pyrrolidone polymeric constituent and from about 0.01 to about 0.5% by weight of said quaternary nitrogen-containing cationic compound, wherein said water-soluble polymeric constituent is present in a quantity larger than said cationic compound, the weight ratio of said water-soluble polymeric constituent to said cationic compound being in the range of from about 30:1 to about 40:1.

4. A detergent composition as in claim 1 wherein said water-soluble cationic compound comprises a $C_{12}$–$C_{16}$ alkylpyridinium chloride.

5. A detergent composition as in claim 1 wherein said water-soluble cationic compound comprises a $C_{12}$–$C_{16}$ alkylpyridinium hydrogen sulfate.

6. A detergent composition as in claim 1 wherein said nonionic surfactant is a reaction product of a $C_8$–$C_{24}$ alcohol and from 2 to 20 moles of an alkylene oxide per mole of the alcohol.

7. A detergent composition as in claim 1 wherein said nonionic surfactant is a reaction product of a $C_8$–$C_{24}$ alcohol selected from the group consisting of a linear or branched, saturated or unsaturated, natural or synthetic alcohol and mixtures thereof, and from 2 to 20 moles of an alkylene oxide per mole of the alcohol.

8. A detergent composition as in claim 7 wherein said alkylene oxide is selected from the group consisting of ethylene oxide, propylene oxide and mixtures thereof.

9. A detergent composition as in claim 1 wherein said vinyl pyrrolidone polymeric constituent comprises homopolymers and/or copolymers of said vinyl pyrrolidone.

10. A detergent composition as in claim 1 comprising (a) from 10 to 20% by weight of a nonionic surfactant prepared by reacting a tallow fatty alcohol with from 5 to 15 moles of ethylene oxide per mole of said alcohol;

(b) from 1 to 4% by weight of polyvinyl pyrrolidone;

(c) from 0.01 to 0.5% by weight of a $C_{12}$–$C_{16}$ alkylpyridinium salt;

(d) from 0.1 to 3% by weight of a foam inhibitor;

(e) from 0.5 to 4% by weight of a silicate selected from the group consisting of sodium and magnesium silicates;

(f) from 10 to 40% by weight of a sodium aluminosilicate;

(g) from 10 to 30% by weight of a sodium perborate;

(h) from 0.5 to 2.5% by weight of a heavy metal complexing agent;

(i) from 0.5 to 3% by weight of a cellulose derivative;

(j) from 0.1 to 1% by weight of an enzyme; and (k) from 0.01 to 0.5% by weight of a perfume.

11. A detergent as in claim 10 wherein said polyvinyl pyrrolidone has a molecular weight of from about 15,000 to about 700,000.

* * * * *